United States Patent
Yano et al.

(10) Patent No.: US 6,485,951 B2
(45) Date of Patent: Nov. 26, 2002

(54) POLYHYDROXYALKANOATE SYNTHASE AND GENE ENCODING THE SAME ENZYME

(75) Inventors: Tetsuya Yano, Atsugi (JP); Takeshi Imamura, Chigasaki (JP); Sakae Suda, Atsugi (JP); Tsutomu Honma, Atsugi (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/821,016

(22) Filed: Mar. 30, 2001

(65) Prior Publication Data

US 2001/0046692 A1 Nov. 29, 2001

(30) Foreign Application Priority Data

Mar. 30, 2000 (JP) .................................. 2000-095004

(51) Int. Cl.$^7$ ............................. C12N 9/04; C07H 21/04
(52) U.S. Cl. ...................................... 435/190; 536/23.2
(58) Field of Search ................................. 435/190, 440, 435/320.1, 252.3; 536/23.2

(56) References Cited

U.S. PATENT DOCUMENTS

| | | | | |
|---|---|---|---|---|
| 4,477,645 | A | 10/1984 | Holmes et al. | 528/361 |
| 5,135,859 | A | 8/1992 | Witholt et al. | 435/135 |
| 5,200,332 | A | 4/1993 | Yamane et al. | 435/135 |
| 5,292,860 | A | 3/1994 | Shiotani et al. | 528/361 |
| 5,849,894 | A | 12/1998 | Clemente et al. | 536/23.2 |
| 5,968,805 | A | * 10/1999 | Doi et al. | 435/252.3 |

FOREIGN PATENT DOCUMENTS

| | | |
|---|---|---|
| EP | 1 120 461 | 8/2001 |
| JP | 5-7492 | 1/1993 |
| JP | 5-93049 | 4/1993 |
| JP | 7-14352 | 1/1995 |
| JP | 7-265065 | 10/1995 |
| JP | 2642937 | 5/1997 |
| JP | 9-191893 | 7/1997 |
| WO | WO 91/00917 | 1/1991 |
| WO | WO 01/11014 | 2/2001 |

OTHER PUBLICATIONS

H. Matsusake et al., "PHA Synthase 1" Retrieved from EBI, Database Accession No. Q9Z3Y1, May 1, 1999 (XP–002176385), Abstract.
H. Matsusake et al., "PHA Synthase 2" Retrieved from EBI, Database Accession No. Q9Z3X9, May 1, 1999 (XP–002176384), Abstract.
H. Matsusake et al., "Pseudomonas sp. 61–3 Genes for PHA Synthase 1, PHA Depolymerase, PHA Synthase 2 and PhaD, Complete CDs" Retrieved from EBI, Database Accession No. AB014758, Dec. 12, 1998 (XP–002176386), Abstract.
Belén García et al., "Novel Biodegradable Aromatic Plastics from a Bacterial Source," 274(41) *J. Biol. Chem.* 29228–28241 (1999).
D.M. Becker et al., "High–Efficiency Transformation of Yeast by Electroporation," 194 *Methods Enzymol.* 182–187 (1990).
H. Ito et al., "Transformation of Intact Yeast Cells Treated with Alkali Cations," 153(1) *J. Bacteriol.* 163–168 (1983).
A. Hinnen et al., "Transformation of Yeast," 75(4) *Proc. Natl. Acad. Sci.* 1929–1933 (1978).
K. Fritzsche et al., "An Unusual Bacterial Polyester With a Phenyl Pendant Group," 191 *Makromol. Chem.* 1957–1965 (1990).
J. Marmur, "A Procedure for the Isolation of Deoxyribonucleic Acid From Micro–Organisms," 3 *J. Mol. Biol.* 208–218 (1961).
*Methods in Enzymology*, vol. 68, p. 253 (1979).
O. Peoples et al., "Poly–β–hydroxybutyrate Biosynthesis in *Alcaligenes eutrophus* H16," 264(26) *J. Biol. Chem.* 15293 (1989).
G. W. Huisman et al., "Metabolism of Poly(3–hydroxyalkanoates) (PHAs) by *Pseudomonas oleovorans*," 266 *J. Biol. Chem.* 2191 (1991).
U. Pieper et al., "Identification, Cloning and Sequence Analysis of the Poly(3–hydroxialkanoic acid) Synthase Gene of the Gram–Positive Bacterium *Rhodococcus ruber*," 96 *FEMS Microbiol. Lett.* 73 (1992).
A. Timm et al., "Cloning and Molecular Analysis of the Poly(3–hydroxyalkanoic acid) Gene Locus of *Pseudomonas aeruginosa* PAO1," 209 *Eur. J. Biochem.* 15 (1992).
H. Matsusaki et al., "Cloning and Molecular Analysis of the Poly)3–hydroxybutyrate) and Poly(3–hydroxybutyrate)–co–3–hydroxyalkanoate) Biosynthesis Genes in Pseudomonas sp. Strain 61–3," 180(24) *J. Bacteriol.* 6459 (1998).

* cited by examiner

*Primary Examiner*—Ponnathapu Achutamurthy
*Assistant Examiner*—Yong Pak
(74) *Attorney, Agent, or Firm*—Fitzpatrick, Cella, Harper & Scinto

(57) ABSTRACT

A novel polyhydroxyalkanoate (PHA) synthase derived from a microorganism capable of producing a PHA having a novel side-chain structure and a DNA encoding the amino acid sequence for the synthase are provided. Two PHA synthase proteins (SEQ ID Nos. 1 and 3) derived from *Pseudomonas jessenii* P161 (FERM BP-7376) and PHA synthase genes encoding these PHA synthases are provided, respectively (SEQ ID Nos. 2 and 4). A recombinant microorganism is endowed with a PHA producing ability.

1 Claim, No Drawings

POLYHYDROXYALKANOATE SYNTHASE AND GENE ENCODING THE SAME ENZYME

BACKGROUND OF THE INVENTION

1. Field of the Invention

This invention relates to a polyhydroxyalkanoate (hereinafter, referred to as a "PHA") synthase, a gene encoding the PHA synthase, a recombinant vector containing the gene, a transformant capable of expressing the PHA synthase which has been transformed by the recombinant vector, a process for producing the PHA synthase utilizing the transformant, and a process for preparing the PHA utilizing the transformant. In particular, this invention relates to a microorganism-derived PHA synthase capable of producing a polyhydroxyalkanoate and a gene encoding the PHA synthase utilized for expressing the PHA synthase by transformation.

2. Related Background Art

There have been reported a number of microorganisms producing poly-3-hydroxybutyric acid (PHB) or another PHA and storing it therein ("Biodegradable Plastic Handbook", edited by Biodegradative Plastic Research Society, NTS Co. Ltd., p.178–197). These polymers may be, as conventional plastics, used for producing a variety of products by, for example, melt-processing. Since they are biodegradable, they have an advantage that they can be completely degraded by microorganisms in the natural environment, and they do not cause pollution due to remaining in the natural environment like many conventional polymer compounds. Furthermore, they are excellently biocompatible, and thus are expected to be used in applications such as a medical soft member.

It is known that a composition and a structure of such a PHA produced by a microorganism may considerably vary depending on the type of a microorganism used for the production, a culture-medium composition and culturing conditions. Investigations have been, therefore, mainly focused on controlling such a composition or structure for the purpose of improving physical properties of a PHA.

For example, Japanese Patent Application Nos. 7-14352 and 8-19227 and Japanese Examined Publication No. 6-15604 described that Alcaligenes eutropus H16 (ATCC No. 17699) and its variants may produce 3-hydroxybutyric acid (3HB) and its copolymer with 3-hydroxyvaleric acid (3HV) with various composition ratios by changing a carbon source during culturing.

Japanese Patent Publication No. 26-42937 discloses that PHA in which a monomer unit is 3-hydroxyalkanoate with 6 to 12 carbon atoms may be produced by supplying a non-cyclic aliphatic hydrocarbon as a carbon source to Pseudomonas oleovorans (ATCC No. 293-47).

Japanese Patent Application Laid-Open No. 5-7492 discloses methods in which Methylobacterium sp., Paracoccus sp., Alcaligenes sp., and Pseudomonas sp. are contacted with a primary alcohol with 3 to 7 carbon atoms to produce a copolymer of 3HB and 3HV.

Japanese Patent Application Laid-Open Nos. 5-93049 and 7-265065 disclose that *Aeromonas caviae* is cultured using oleic acid or olive oil as a carbon source to produce a two-component copolymer of 3HB and 3-hydroxyhexanoic acid (3HHx).

Japanese Patent Application Laid-Open No. 9-191893 discloses that Comamonas acidovorans IF013852 is cultured using gluconic acid and 1,4-butanediol as carbon sources to produce a polyester having 3HB and 4-hydroxybutyric acid as monomer units.

Furthermore, it is reported that certain microorganisms produce PHAs having a variety of substituents such as unsaturated hydrocarbon, ester, aryl (aromatic), and cyans groups, halogenated hydrocarbon and epoxide. Recently, there have been attempts for improving physical properties of a PHA produced by a microorganism using such a procedure. For example, Makromol. Chem., 191, 1957–1965 (1990); Macromolecules, 24, 5256–5260 (1991); and Chirality, 3, 492–494 (1991) describe production of a PHA comprising 3-hydroxy-5-phenylvaleric acid (3HPV) as a monomer unit by *Pseudomonas oleovorans*, where variations in polymer physical properties probably due to the presence of 3HPV were observed.

As described above, microorganism-produced PHAs with various combinations of composition and structure have been obtained by varying factors such as the type of a microorganism used, a culture medium composition and culturing conditions. Each microorganism has an intrinsic PHA synthase with a substrate specificity which is significantly different from others. Thus, it has been difficult to produce PHAs comprising different monomer units suitable to a variety of applications using known microorganisms or PHA synthases in such known microorganisms.

Meanwhile, as described above, a PHA having a variety of substituents in its side chains may be expected to be a "functional polymer" having significantly useful functions and properties owing to the properties of the introduced substituents. It is, therefore, extremely useful and important to search and develop a microorganism which can produce and store a very useful polymer having both such functionality and biodegradability. Furthermore, identification of a PHA synthase involved in production of the highly useful PHA and obtaining a gene encoding the PHA synthase may allow us to produce a novel transformed microorganism capable of producing a desired PHA. That is, constructing a recombinant vector comprising a gene encoding a PHA synthase and providing a microorganism transformed by the recombinant vector may allow us to prepare a PHA using the transformed microorganism or to express a recombinant type of PHA synthase. As described above, it may be important that a transformed microorganism is used to prepare a desired PHA for providing a highly useful tool for improving a productivity for the PHA and for promoting utilization of the PHA.

SUMMARY OF THE INVENTION

Objects of this invention which can solve the above problems are to search a novel microorganism capable of producing and storing in microorganisms a PHA having a novel side-chain structure, to identify an enzyme protein related to the ability of producing the novel PHA, i.e., a novel PHA synthase, and to determine a gene encoding its amino acid sequence. More specifically, an object of the present invention is to provide a novel PHA synthase derived from a microorganism producing a PHA having a novel side chain structure and a DNA encoding its amino acid sequence. Another object of this invention is to provide a recombinant vector to which a DNA encoding an available PHA synthase is introduced and which is used for transformation of a microorganism and a transformed microorganism produced using the recombinant vector. A further object of this invention is to provide a process for expressing and producing a recombinant PHA synthase in the transformed microorganism and a process for preparing a desired PHA using the transformed microorganism.

Still another object of this invention is to provide a modified PHA synthase in which its amino acid sequence is modified as long as an enzyme activity is not affected in expression of the recombinant PHA synthase in the transformed microorganism as described above and a DNA encoding the modified amino acid sequence.

For developing a PHA having a novel side-chain structure useful as, for example, a device material or a medical material aiming at solving the above problems, the inventors have searched a novel microorganism capable of producing and storing the desired PHA therein. Additionally, the inventors have intensely investigated selected novel microorganisms producing a novel PHA for identifying a PHA synthase involved in production of the novel PHA and for obtaining a gene encoding the PHA synthase. Furthermore, the inventors have conducted investigation for constructing a recombinant vector with a gene for the obtained PHA synthase, transforming a host microorganism using the recombinant vector, expressing a recombinant PHA synthase in the transformed microorganism obtained and determining production of the desired PHA.

In the course of the above investigation, the inventors synthesized 5-(4-fluorophenyl) valeric acid (FPVA) represented by formula (II):

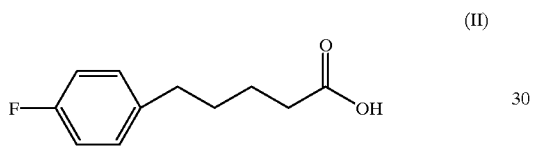

(II)

and separated from a soil a novel microorganism capable of converting the above compound (II) as a starting material (substrate) into corresponding 3-hydroxy-5-(4-fluorophenyl)valeric acid (3HFPV) represented by formula (III):

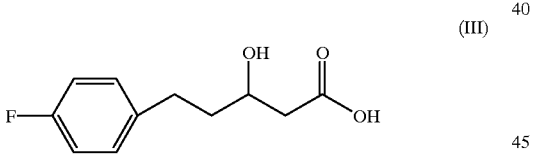

(III)

and producing and storing a novel PHA with a monomer unit represented by formula (I):

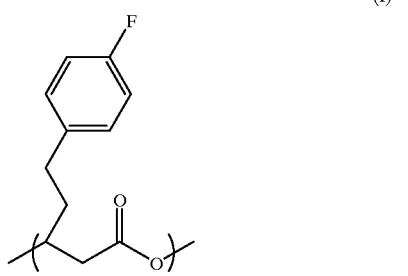

(I)

derived from 3HFPV. The novel microorganism separated is designated as P161 strain. The inventors have also found that in addition to the above enzymatic activity for converting FPVA into 3HFPV, the P161 strain may also use 4-phenoxybutyric acid (PXBA) represented by formula (IV):

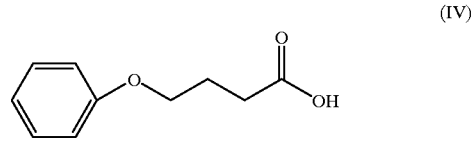

(IV)

as a starting material (substrate) to convert it into 3-hydroxy-4-phenoxybutyric acid (3HPxB) represented by formula (V):

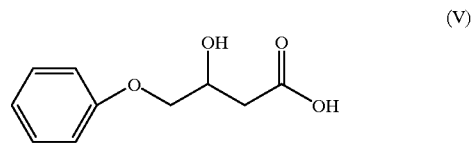

(V)

and to produce and store a PHA with a monomer unit represented by formula (VI):

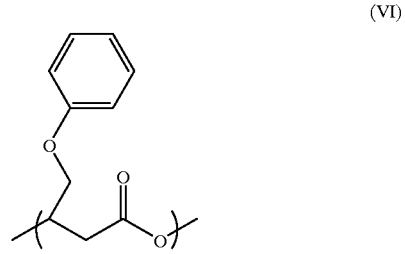

(VI)

derived from 3HPxB. There have been no reports for microbial production of a PHA comprising 3HPxB as a monomer unit using PXBA as a substrate or for microbial production of a PHA comprising 3HPxB as a sole phenoxy-containing monomer unit.

An example of a microorganism capable of producing and storing a PHA with a monomer unit represented by formula (VI) derived from 3HPxB using a substrate other than PxBA is Pseudomonas oleovorans using 8-phenoxyoctanoic acid (PxOA) as a substrate described in Macromolecules, 29, 3432–3435, 1996. In *Pseudomonas oleovorans*, 8-phenoxyoctanoic acid (PxOA) is used as a substrate, which is totally different from the enzymatic reaction in P161 strain where PxBA is used as a substrate to produce a PHA with a monomer unit represented by formula (VI) derived from a corresponding 3HPxB. In addition, for the composition of a PHA produced, the reported process using *Pseudomonas oleovorans* provides a copolymer consisting of three monomer units, i.e., 3-hydroxy-8-phenoxyoctanoic acid corresponding to PxOA as a substrate, 3-hydroxy-6-phenoxyhexanoic acid as a byproduct derived from a metabolite of the substrate, and the desired 3HPxB. On the other hand, a process where P161 strain acts on the substrate PxBA provides a PHA with 3HPxB derived from PXBA as a sole phenoxy-containing monomer unit. Taking the compositions of the PHAs also into consideration, it seems that there is fundamental difference in substrate specificity of a PHA synthase between *Pseudomonas oleovorans* used in the above process reported and P161 strain. That is, a PHA synthase produced by P161 strain is more preferable for production of a PHA with 3HPxB as a monomer unit.

Furthermore, the inventors have found that P161 strain can use 6-phenylhexanoic acid (PHxA) represented by formula (VII):

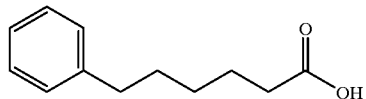
(VII)

as a starting material (substrate) to convert it into corresponding 3-hydroxy-6-phenylhexanoic acid (3HPHx) represented by formula (VIII):

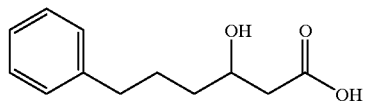
(VIII)

and to produce and store a novel PHA with a monomer unit represented by formula (IX):

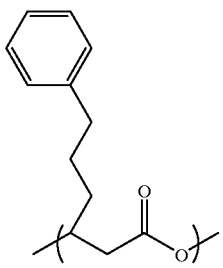
(IX)

derived from 3HPHx.

Microbiological properties of P161 strain are as follows.
<Microbiological Properties of P161 Strain>
Morphologic Properties
Cell shape and size: Sphere, φ0.6 μm
Bacilliform, 0.6 μm×1.5 to 2.0 μm
Cell polymorphism: Yes (elongation)
Motility: Yes
Sporulation: No
Gram stainability: Negative
Colonization: Circular, smooth in the overall periphery, low convex, smooth surface, pale yellow
Physiological Properties
Catalase: Positive
Oxidase: Positive
O/F test: oxidized form
Reduction of a nitrate: Positive
Indole formation: Negative
Acidification of dextrose: Negative
Arginine dihydrolase: Positive
Urease: Negative
Esculin hydrolysis: Negative
Gelatin hydrolysis: Negative
β-Galactosidase: Negative
Fluorochrome production on King's B agar: Positive
Substrate Assimilation Ability
Dextrose: Positive
L-Arabinose: Positive
D-Mannose: Positive
D-Mannitol: Positive
N-Acetyl-D-glucosamine: Positive
Maltose: Negative
Potassium gluconate: Positive
n-Capric acid: Positive
Adipic acid: Negative
dl-Malic acid: Positive
Sodium citrate: Positive
Phenyl acetate: Positive From these microbiological properties, the inventors have attempted to categorize P161 strain according to Bergey's Manual of Systematic Bacteriology, Volume 1 (1984) and Bergey's Manual of Determinative Bacteriology 9th ed. (1994) to determine that the strain belongs to Pseudomonas sp. Its taxonomic position could not been determined from these microbiological properties.

Thus, for categorizing P161 strain from its genetic properties, the inventors sequenced its 16S rRNA (SEQ ID NO. 5) and compared its homology with the sequence of a 16S rRNA in a known Pseudomonas sp. microorganism. The results indicate quite higher homology in a 16S rRNA sequence between P161 strain and a known *Pseudomonas jessenii*. Furthermore, microbiological properties described for the known *Peudomonas jessenii* in System. Appl. Microbiol., 20, 137–149 (1997) and System. Appl. Microbiol., 22, 45–58 (1999) was compared with those for P161 strain and observed considerable homology. From these results, it was judged to be proper to categorize P161 strain in *Pseudomonas jessenii*, and thus it is designated as *Pseudomonas jessenii* P161. There have been no reports on a strain in *Pseudomonas jessenii* capable of producing a PHA as exhibited by P161 strain. The inventors have, therefore, determined that P161 strain is a novel microorganism. The applicant deposited *Pseudomonas jessenii* P161 to Patent Microorganism Depository Center in the National Institute of Bioscience and Human Technology, Agency of Industrial Science and Technology, Ministry of International Trade and Industry, under the deposition number of FERM P-17445. P161 strain has been internationally deposited on the basis of the Budapest Treaty, and its international accession number is "FERM BP-7376".

The inventors achieved cloning a gene for a PHA synthase from the novel microorganism P161 strain and sequenced the gene. The inventors also determined an amino acid sequence for the PHA synthase encoded by the gene. Based on the above observation, the present invention was achieved.

Specifically, a PHA synthase of the present invention is a polyhydroxyalkanoate synthase having an amino acid sequence of SEQ ID NO. 1 or 3. Furthermore, the PHA synthase of the present invention may be a PHA synthase substantially retaining the amino acid sequence of SEQ ID NO. 1 and having a modified amino acid sequence where amino acids are deleted, substituted or added as long as it does not deteriorate an activity as the polyhydroxyalkanoate synthase, or a PHA synthase substantially retaining the amino acid sequence of SEQ ID NO. 3 and having a modified amino acid sequence where amino acids are deleted, substituted or added as long as it does not deteriorate activity as the polyhydroxyalkanoate synthase.

A PHA synthase gene of the present invention is a gene for a polyhydroxyalkanoate synthase comprising a DNA encoding the amino acid sequence of SEQ ID NO. 1 or the sequence of its modified amino acid, or a gene for a polyhydroxyalkanoate synthase comprising a DNA encoding the amino acid sequence of SEQ ID NO. 3 or the sequence of its modified amino acid. Embodiments of a PHA synthase gene of the present invention derived from a genome gene in P161 strain include a PHA synthase gene comprising a DNA sequence of SEQ ID NO. 2 as a DNA encoding the amino acid sequence of SEQ ID NO. 1 and a PHA synthase gene comprising a DNA sequence of SEQ ID NO. 4 as a DNA encoding the amino acid sequence of SEQ ID NO. 3.

This invention also provides a recombinant vector comprising a gene DNA encoding the above amino acid sequence as a polyhydroxyalkanoate synthase gene. This invention also provides a transformed microorganism transformed by introducing a recombinant vector adapted to a host.

The present invention also provides a process for preparing a polyhydroxyalkanoate comprising the steps of culturing the transformed microorganism to which a recombinant vector has been introduced in a culture medium containing a substrate for a polyhydroxyalkanoate synthase and collecting the polyhydroxyalkanoate from the culture preparation. The present invention also provides a process for producing a polyhydroxyalkanoate comprising the steps of culturing the transformed microorganism to which a recombinant vector has been introduced and making the transformed microorganism produce the polyhydroxyalkanoate.

A preferable process for producing a polyhydroxyalkanoate may utilize substrate specificity characteristic of a polyhydroxyalkanoate synthase derived from P161 strain: for example, preparation of a polyhydroxyalkanoate comprising a monomer unit represented by formula (I) derived from 3HFPV utilizing the above transformed microorganism; preparation of a polyhydroxyalkanoate comprising a monomer unit represented by formula (VI) derived from 3HPxB, or preparation of a polyhydroxyalkanoate comprising a monomer unit represented by formula (IX) derived from 3HPHx.

A PHA synthase and a gene encoding the PHA synthase of the present invention are derived from a novel microorganism, Pseudomonas jessenii P161 strain and exhibits such substrate specificity that it selectively produces a PHA comprising a monomer unit having a novel side chain structure. A recombinant vector comprising the PHA synthase gene and a microorganism transformed by the recombinant vector are capable of producing a PHA exhibiting substrate specificity similar to Pseudomonas jessenii P161. Thus, a PHA synthase gene of this invention encodes an enzyme which permits preparation of a PHA selectively comprising a monomer unit having a novel side-chain structure and allows us to create a transformed microorganism useful for preparing a PHA having various useful physical properties which may be expected to be applied to a functional polymer.

DETAILED DESCRIPTION OF THE PREFERRED EMBODIMENTS

A PHA synthase of this invention is an enzyme protein derived from a novel microorganism isolated by the present inventors, Pseudomonas jessenii P161 (FERM BP-7376). Specifically, it can covert 5-(4-fluorophenyl)valeric acid (FPVA) into corresponding 3-hydroxy-5-(4-fluorophenyl) valeric acid (3HFPV), 4-phenoxybutyric acid (PXBA) into corresponding 3-hydroxy-4-phenoxybutyric acid (3HPxB) or 6-phenylhexanoic acid (PHxA) into corresponding 3-hydroxy-6-phenylhexanoic acid (3HPHx) and thus has enzymatic activity involved in production of a PHA comprising a corresponding monomer unit.

A PHA synthase and a gene encoding the enzyme of this invention will be more specifically described.

From P161 strain, the inventors have cloned a gene translated into a PHA synthase which exhibits the above substrate specificity, to determine the presence of a PHA synthase comprising at least two amino acid sequences. Specifically, a PHA synthase of this invention in a chromogene in P161 strain comprises two enzymes, i.e., a PHA synthase comprising the amino acid sequence of SEQ ID NO. 1 encoded by a DNA having the sequence of SEQ ID NO. 2 and a PHA synthase comprising the amino acid sequence of SEQ ID NO. 3 encoded by a DNA having the sequence of SEQ ID NO. 4. Gene DNAs of the sequences of SEQ ID NOs. 2 and 4 may be cloned by the following procedure.

Since a PHA synthase is an enzyme protein translated from a chromogene, a chromosome DNA containing a desired PHA synthase is first obtained. A chromosome DNA may be separated from P161 strain cells by a known separation method. For example, P161 strain is cultured in a LB medium or an M9 medium supplemented with an appropriate carbon source, disrupt and treated as described by, for example, Marmer et al. in Journal of Molecular Biology, Vol. 3, p. 208 (1961) to prepare a chromosome DNA.

Then, a gene library is prepared from the chromosome DNA thus obtained. The chromosome DNA is degraded using an appropriate restriction enzyme (e.g., Sau3AI) and a fragment with a proper length is ligated with a ligatable vector truncated with a restriction enzyme (e.g., BamHI) to prepare a gene library.

Depending on a vector used in preparing a library, a proper fragment length varies, e.g., about 4000 to 25000 bps for a usual plasmid vector and about 15000 to 30000 bps for a cosmid or phage vector. A proper length of DNA fragment may be collected by a known method such as a method using a sucrose density gradient or using an agarose gel described in Molecular Cloning, Cold Spring Harbor Laboratory (1982).

Since E. coli is used as a host microorganism in a gene library, a vector is a phage vector or plasmid vector which can autonomously grow in the host microorganism (E. coli). Examples of phage or cosmic vectors generally used include pWE15, M13, λEMBL3, λEMBL4, λFIXII, λDASHII, λZAPII, λgt10, λgt11, Charon4A and Charon21A. Examples of frequently used plasmid vectors include pBR, pUC, pBluescriptII, pGEM, pTZ and pET groups. In addition to E. coli, various shuttle vectors may be used, e.g., vectors which may automonouosly grow in a plurality of host microorganisms such as Pseudomonas sp. Again, these vectors may be, depending on a chromosome DNA to be ligated to them, truncated with a proper restriction enzyme to provide a desired fragment.

A chromosome DNA fragment may be ligated with a vector fragment using a DNA ligase. For example, a commercially available ligation kit (Takara Shuzo Co., Ltd., etc.) may be used. Thus, for example, various chromosome DNA fragments may be ligated with a plasmid vector fragment to prepare a mixture of recombinant plasmids comprising various DNA fragments (hereinafter, referred to as a "gene library").

In addition to a method using a proper length of chromosome DNA fragment, a gene library may be prepared by a method that all mRNAs are extracted from P161 strain, purified and used for preparation of a cDNA fragment using a reverse transcriptase as described in Molecular Cloning, Cold Spring Harbor Laboratory, 1982. Alternatively, a prepared vector is used in a gene library to transform or transduce to E. coli, and then the host E. coli is cultured to amplify the gene library to a large amount as described in Molecular Cloning, Cold Spring Harbor Laboratory, 1982.

A recombinant vector comprising a gene DNA fragment may be introduced into a host microorganism by a known method. For example, when using *E. coli* as a host microorganism, a recombinant plasmid vector may be introduced using a calcium chloride method (Journal of Molecular Biology, Vol. 53, p. 159 (1970)), a rubidium chloride method (Methods in Enzymology, Vol. 68, p. 253 (1979)), electroporation (Current Protocols in Molecular Biology, Vol. 1, p. 1.8.4 (1994)). When using a cosmid vector or phage vector, transduction in a host *E. coli* may be conducted using in vitro packaging (Current Protocols in Molecular Biology, Vol. 1, p. 5.7.1 (1994)). Alternatively, conjugational transfer with a strain retaining a recombinant vector may be utilized to prepare a strain retaining a vector.

Then, from the gene library, a probe is prepared for obtaining a DNA fragment comprising a PHA synthase gene of P161 strain.

Some base sequences have been reported for PHA synthase genes in known microorganisms; for example, Peoples, O. P. and Sinskey, A. J., J. Biol. Chem., 264, 15293 (1989); Huisman, G. W. et al., J. Biol. Chem., 266, 2191 (1991); Pieper, U. et al., FEMS Microbiol. Lett., 96, 73 (1992); Timm, A. and Steinbuchel, A., Eur. J. Biochem., 209, 15(1992); Matsusaki, H. et al., J. Bacteriol., 180, 6459 (1998). These reported sequences are compared to select a region where a sequence is preserved to a higher degree and thus to design an oligonucleotide for a primer used in polymerase chain reaction (hereinafter, referred to as "PCR"). Such oligonucleotides for a primer utilizing a common feature of PHA synthase genes include, but not limited to, a sequence described in Timm, A. and Steinbuchel, A., Eur. J. Biochem., 209, 15 (1992). An oligonucleotide may be synthesized using, for example, a commercially available DNA synthesizer such as Custom Synthesis Service, Amersham-Pharmacia Biotech, depending on a designed sequence.

For a PHA synthase gene derived from P161 of this invention, synthetic DNAs having the sequences of SEQ ID NOs. 6 and 7 were designed.

Then, the designed oligonucleotide as a primer is subject to polymerase chain reaction (PCR) using a chromosome DNA in P161 strain as a template to obtain a PCR amplified fragment. The PCR amplified fragment, which is derived from the primer, comprises a sequence common in PHA synthase genes at both ends. A partial sequence derived from the PHA synthase gene itself in P161 strain as a template is contained between sequences complementary to the primer at both ends.

The PCR amplified fragment obtained is, therefore, almost 100% homologous to the PHA synthase gene in P161 strain and is expected to exhibit a higher S/N ratio as a probe in colony hybridization. In addition, it may facilitate stringency control of hybridization.

The above PCR amplified fragment is labeled with an appropriate reagent and used as a probe to colony-hybridize the above chromosome DNA library for selecting a recombinant *E. coli* strain retaining the PHA synthase gene (Current Protocols in Molecular Biology, Vol. 1, p. 6.0.3 (1994)). For example, the PCR amplified fragment may be labeled using a common detection system using a labeled enzyme or a commercially available kit such as AlkPhos-Direct (Amersham-Pharmacia Biotech).

A recombinant *E. coli* strain retaining a gene fragment comprising a PHA synthase gene may be selected by, in addition to the above method using a gene type, a method using a phenotype where PHA synthesis is directly evaluated. Specifically, in expression of a PHA synthase from a retained PHA synthase gene in a recombinant *E. coli* strain, PHA is produced by the PHA synthase. PHA synthesis may be detected to select a recombinant *E. coli* strain in which the PHA synthase is expressed. PHA synthesis may be detected by, for example, staining with Sudan Black B (Archives of Biotechnology, Vol. 71, p. 283 (1970)) or determination of PHA accumulation by phase contrast microscopy.

A plasmid is collected from a recombinant *E. coli* selected by any of the above methods using an alkali method (Current Protocols in Molecular Biology, Vol. 1, p. 1.6.1 (1994)). The collected plasmid may be used to provide a DNA fragment comprising a PHA synthase gene or multiple DNA fragments partially containing a PHA synthase gene. The DNA fragment obtained may be sequenced by, for example, the Sanger's sequencing method (Molecular Cloning, Vol. 2, p. 13.3 (1989). Specifically, it may be conducted by a dye-primer method or a dye-terminator method using an automatic sequencer such as DNA Sequencer 377A (Parkin Elmer). Since the sequence of the vector itself in which the DNA fragment has been incorporated is known, the sequence of the DNA fragment cloned therein may be unequivocally analyzed.

After sequencing all the obtained DNA fragments comprising a PHA synthase gene, hybridization may be conducted using a DNA fragment prepared by an appropriate method such as chemical synthesis, PCR using a chromosome DNA as a template or degradation of a DNA fragment comprising the sequence with a restriction enzyme as a probe to provide a PHA synthase gene DNA of this invention.

The inventors have selected a gene translated into a PHA synthase exhibiting the above substrate specificity from P161 strain according to the above procedure to find a PHA synthase comprising at least two amino acid sequences. Specifically, the inventors have found a PHA synthase gene collected from the chromosome DNA of P161 strain and comprising the sequence of SEQ ID NO. 2 and a PHA synthase encoded by the gene and comprising the amino acid of SEQ ID NO. 1 as well as a PHA synthase gene comprising the sequence of SEQ ID NO. 4 and a PHA synthase encoded by the gene and comprising the amino acid of SEQ ID NO. 3.

A PHA synthase gene of the present invention may include a degenerated isomer encoding the same polypeptide which has the same amino acid sequence and is different in a degeneration codon. More specifically, it also includes a degenerated isomer by selection and conversion of a more frequently used degenerated codon encoding the same amino acid depending on a host. Besides the PHA synthase comprising the amino acid sequence of SEQ ID NO. 1 inherent in P161 strain and the PHA synthase comprising the amino acid sequence of SEQ ID NO. 3, a PHA synthase of this invention may have mutation such as deletion, substitution and addition for several amino acids as long as its PHA producing activity and substrate specificity may not be deteriorated or the amino acid sequence may be maintained. Mutation such as deletion, substitution and addition may be introduced by a site mutation introduction technique based on a PHA synthase gene inherent in P161 strain having the sequence of SEQ ID NO. 2 or 4 (Current Protocols in Molecular Biology Vol. 1, p. 8.1.1 (1994)).

A recombinant vector of the present invention is used in an application where a recombinant PHA synthase of this invention is expressed using Pseudomonas sp. or a microorganism such as E. coli as a host. It is, therefore, preferable that the recombinant vector of this invention itself can autonomously replicate in a host used while comprising a promoter for expression, a PHA synthase gene DNA of this invention and a transcription termination sequence suitable to the host. In addition, it is preferable that after introducing the recombinant vector, a vector comprising various marker genes used for its selection is used.

Expression vectors suitable to various types of bacterial hosts such as Pseudomonas sp. and E. coli include pLA2917 (ATCC37355) having a RK2 replication origin which may be replicated and retained by a range of hosts or pJRD215 (ATCC37533) having a RSF1010 replication origin. Without being limited to these, any vector having a replication origin which may be replicated and retained by a range of hosts may be used. Any promoter which may be expressed in a bacterium as a host may be used; for example, promoters derived from E. coli, a phage, etc. such as trp, trc, tac, lac, PL, PR, T7 and T3 promoters.

When using a yeast as a host, an expression vector may be Yep13, Ycp50, pRS or pYEX vector. A promoter may be, for example, GAL or AOD promoter.

A transformed microorganism of this invention may be produced by introducing a recombinant vector of this invention into a host suitable to an expression vector used during preparing the recombinant vector. Examples of bacteria which may be used as a host include Esherichia sp., Pseudomonas sp., Ralstonia sp., Alcaligenes sp., Comamonas sp., Burkholderia sp., Agrobacterium sp., Flabobacterium sp., Vibrio sp., Enterobacter sp., Rhizobium sp., Gluconobacter sp., Acinetobacter sp., Moraxella sp., Nitrosomonas sp., Aeromonas sp., Paracoccus sp., Bacillus sp., Clostridium sp., Lactobacillus sp., Corynebacterium sp., Arthrobacter sp., Achromobacter sp., Micrococcus sp., Mycobacterium sp., Streptococcus sp., Streptomyces sp., Actinomyces sp., Norcadia sp. and Methylobacterium sp. A recombinant DNA may be introduced into a bacterium by an appropriate technique such as the above calcium chloride method and electroporation.

Besides the above bacteria, yeasts and molds such as Saccharomyces sp. and Candida sp. may be used as a host. A recombinant DNA may be introduced into an yeast by, for example, electroporation (Methods Enzymol., 194, 182–187 (1990)), a spheroplast method (Proc. Natl. Acad. Sci. USA, 84, 1929–1933 (1978)) and a lithium acetate method (J. Bacteriol., 153, 163–168 (1983)).

A PHA synthase of this invention may be prepared by culturing a transformant of this invention prepared by the above procedure and making a corresponding PHA synthase gene in an introduced expression vector producing the synthase as a recombinant protein. The PHA synthase of this invention is produced and accumulated in the culture (cultured bacterium or culture supernatant) and separated from the culture to be used for production of a recombinant enzyme protein. For this purpose, a transformant of this invention may be cultured by a usual procedure used for culturing a host. Culturing may be conducted by any of common methods used for culturing a microorganism such as batch, flow batch, continuous culturing and reactor styles. This culturing may be conducted by using, for example, a medium containing an inducer for expressing the above polyhydroxyalkanoate synthase gene.

For a transformant obtained using a bacterium such as E. coli as a host, a medium used for culturing may be a complete medium or synthetic medium such as LB medium and M9 medium. A microorganism may be grown by aerobically culturing at a culturing temperature of 25 to 37° C. for 8 to 72 hours. Then, the bacteria are collected for obtaining a PHA synthase accumulated in them. Examples of a carbon source for the microorganism include sugars such as glucose, fructose, sucrose, maltose, galactose and starches; lower alcohols such as ethanol, propanol and butanol; polyalcohols such as glycerol; organic acids such as acetic acid, citric acid, succinic acid, tartaric acid, lactic acid and gluconic acid; and aliphatic acids such as propionic acid, butanoic acid, pentanoic acid, hexanoic acid, heptanoic acid, octanoic acid, nonanoic acid, decanoic acid, undecanoic acid and dodecanoic acid.

Examples of a nitrogen source include ammonia; ammonium salts such as ammonium chloride, ammonium sulfate and ammonium phosphate; and natural product derivatives such as peptone, meat extract, yeast extract, malt extract, casein decomposition products and corn steep liquor. Examples of an inorganic material include potassium dihydrogen phosphate, potassium monohydrogen phosphate, magnesium phosphate, magnesium sulfate and sodium chloride. The culture medium may contain an antibiotic such as kanamycin, ampicillin, tetracyclin, chloramphenicol and streptomycin, depending on, for example, the type of a drug resistance gene used as a marker gene.

When using an inducible promoter in an expression vector, expression may be enhanced by adding a proper inducer depending on the type of the promoter during culturing a transformed microorganism. For example, the inducer may be isopropyl-β-D-thiogalactopyranoside (IPTG), tetracyclin or indoleacrylic acid (IAA).

A PHA synthase may be separated and purified by centrifuging and collecting a culture obtained and processing it by a technique such as affinity chromatography, cation or anion exchange chromatography and gel filtration alone or in combination as appropriate. Whether a purified material is a desired enzyme is determined by a usual method such as SDS polyacrylamide gel electrophoresis and Western blotting.

This invention is not limited to the procedures as described above for culturing of a transformed microorganism of this invention, production of a PHA synthase by the transformed microorganism of this invention and accumulating it in bacterial cells, and collection and purification of the PHA synthase from the cells.

A transformed microorganism of this invention may be used for expressing a recombinant PHA synthase to produce a desired PHA. For example, the microorganism may be cultured under the above culturing conditions to produce a recombinant PHA synthase while a substrate corresponding to the desired PHA on which the PHA synthase acts is added to a medium. Most conveniently, the PHA may be collected from the culture and the producing bacteria by extraction with an organic solvent commonly used such as chloroform. In an environment where using an organic solvent such as chloroform is undesirable, the culture may be treated a surfactant such as SDS, an enzyme such as lysozyme, or an agent such as EDTA, sodium hypochlorite and ammonia to remove bacterium components other than the PHA for collecting the PHA. This invention is not limited to the above procedures for culturing of a transformed microorganism of this invention for production of a PHA, production of a PHA by and accumulation thereof in a cultured microorganism, and collection of the PHA from a recombinant microorganism.

EXAMPLES

This invention will be more specifically described with reference to Examples, although these Examples are illustrated as the best embodiments of this invention and do not limit the technical range of this invention.

Example 1

Cloning of a PHA synthase Gene of P161 Strain

P161 strain was cultured in 100 mL of LB medium (1% polypeptone, 0.5% yeast extract, 0.5% sodium chloride, pH 7.4) at 30° C. overnight and then a chromosome DNA was separated and collected as described by Marmer. The obtained chromosome DNA was completely digested using a restriction enzyme BglII. A vector pUC18 was cleaved with a restriction enzyme BamHI. After dephosphorylation of the terminals (Molecular Cloning, Vol. 1, p. 5.7.2 (1989), Cold Spring Harbor Laboratory), the cleaved site of the vector (cloning site) and the chromosome DNA fragment after BglII complete digestion were ligated using a DNA ligation kit Ver. II (Takara Shuzo Co., Ltd.). The plasmid vector in which the chromosome DNA fragment was integrated was used to transform *Escheichia coli* HB101 for preparing a chromosome DNA library for P161 strain.

Then, in order to select a DNA fragment comprising a PHA synthase gene of P161 strain, a probe for colony hybridization was prepared. An oligonucleotide consisting of the sequences of SEQ ID NOs. 6 and 7 (Amersham-Pharmacia Biotech) was prepared and used as a primer for PCR using the chromosome DNA as a template. A PCR-amplified DNA fragment was used as a probe. Labeling of the probe was conducted using a commercially available labeling enzyme system AlkPhosDirect (Amersham-Pharmacia Biotech). The labeled probe thus obtained was used to select an *E. coli* strain containing a recombinant plasmid comprising the PHA synthase gene from the chromosome DNA library of P161 strain by colony hybridization. From the selected strain, the plasmid was collected by an alkali method to prepare a DNA fragment comprising a PHA synthase gene.

The gene DNA fragment thus obtained was recombined in a vector pBBR122 (Mo BiTec) comprising a wide host range of replication region which did not belong to IncP, IncQ or IncW in an incompatible group. The recombinant plasmid was transformed in *Pseudomonas jessenii* P161m1 strain (a strain depleted of PHA synthesizing ability) by electroporation, and then the P161m1 strain regained PHA synthesizing ability and exhibited complementarity. It demonstrates that the selected gene DNA fragment comprises a region of a PHA synthase gene translatable into a PHA synthase in Pseudomonas jessenii P161m1.

The DNA fragment comprising a PHA synthase gene was sequenced by the Sanger's sequencing method. It was thus found that the determined sequence comprised the sequences of SEQ ID NOs. 2 and 4 each of which encoded a peptide chain. As described below, it was determined that both proteins consisting of a peptide chain had enzyme activity and that the sequences of SEQ ID NOs. 2 and 4 were therefore PHA synthase genes. Specifically, it was found that the sequences of SEQ ID NOs. 2 and 4 encoded the amino acid sequences of SEQ ID NOs. 1 and 3, respectively, and that a protein comprising one of these amino acid sequences alone could produce a PHA.

Example 2

Recombination of a PHA Synthase Gene of P161 Strain to an Expression Vector

A PHA synthase gene having the sequence of SEQ ID NO. 2 was PCRed using a chromosome DNA as a template to reproduce the whole length of a PHA synthase gene. An oligonucleotide having a sequence which was an upstream primer to the sequence of SEQ ID NO. 2 and had a sequence upstream of its initiation codon (SEQ ID NO. 8) and an oligonucleotide having a sequence which was a downstream primer to the sequence of SEQ ID NO. 2 and had a sequence downstream of its termination codon (SEQ ID NO. 9) were designed and prepared (Amersham-Pharmacia Biotech). Using these oligonucleotides as a primer, PCR was conducted to amplify the whole length of the PHA synthase gene (LA-PCR kit; Takara Shuzo Co., Ltd.).

Likewise, a PHA synthase gene having the sequence of SEQ ID NO. 4 was PCRed using a chromosome DNA as a template to reproduce the whole length of a PHA synthase gene. An oligonucleotide having a sequence which was an upstream primer to the sequence of SEQ ID NO. 4 and had a sequence upstream of its initiation codon (SEQ ID NO. 10) and an oligonucleotide having a sequence which was a downstream primer to the sequence of SEQ ID NO. 4 and had a sequence downstream of its termination codon (SEQ ID NO. 11) were designed and prepared (Amersham-Pharmacia Biotech). Using these oligonucleotides as a primer, PCR was conducted to amplify the whole length of the PHA synthase gene (LA-PCR kit; Takara Shuzo Co., Ltd.).

Each of the obtained PCR amplified fragment containing the whole length of the PHA synthase gene was completely digested using a restriction enzyme HindIII. Separately, an expression vector pTrc99A was also truncated with a restriction enzyme HindIII and dephosphorylated (Molecular Cloning, Vol. 1, p. 5.7.2 (1989), Cold Spring Harbor Laboratory). To the truncated site of the expression vector pTrc99A was ligated the DNA fragment comprising the whole length of the PHA synthase gene from which unnecessary sequences had been removed at both ends, using a DNA ligation kit Ver. II (Takara Shuzo Co., Ltd.).

Using the recombinant plasmids obtained, *Escherichia coli* HB101 (Takara Shuzo Co., Ltd.) was transformed by a calcium chloride method. The recombinants were cultured, and the recombinant plasmids were amplified and collected individually. The recombinant plasmid retaining the gene DNA of SEQ ID NO. 2 was designated pP161-C1 (derived from SEQ ID NO. 2) while the recombinant plasmid retaining the gene DNA of SEQ ID NO. 4 was designated pP161-C2 (derived from SEQ ID NO. 4).

Example 3

PHA Production (1) Using a PHA Synthase Gene Recombinant *E. coli*

Using the recombinant plasmids obtained in Example 2, pP161-C1 (derived from SEQ ID NO. 2) and pP161-C2

(derived from SEQ ID NO. 4), an *Escherichia coli* HB101fB (fadB deficient strain) was transformed by a calcium chloride method to prepare recombinant *E. coli* strains retaining the recombinant plasmid, pP161-C1 and pP161-C2 recombinant strains, respectively.

Each of the pP161-C1 and pP161-C2 recombinant strains was inoculated to 200 mL of M9 medium containing 0.5% yeast extract and 0.1% FPVA, and the medium was shaken at 37° C. with a rate of 125 strokes/min. After 24 hours, the cells were collected by centrifugation, washed once with cold methanol and lyophilized.

The lyophilized pellet was suspended in 100 mL of chloroform and the suspension was stirred at 60° C. for 20 hours to extract a PHA. After filtering the extract through a membrane filter with a pore size of 0.45 μm, the filtrate was concentrated by rotary evaporation. Then, the concentrate was re-suspended in cold methanol and the precipitant was collected and dried in vacuo to provide a PHA. The PHA thus obtained was subject to methanolysis as usual and analyzed using a gas chromatography-mass spectrometry apparatus (GC-MS, Shimadzu QP-5050, EI technique) to identify methyl-esterified PHA monomer units. Table 1 shows together a cell dry weight, a polymer dry weight for a collected PHA, a polymer yield per a cell (polymer dry weight/cell dry weight) and identities of monomer units for each strain.

produce PHA synthases having the amino acid sequences of SEQ ID NOs. 1 and 3 translated from the PHA synthase genes comprising the sequences of SEQ ID NOs. 2 and 4, respectively, both strains similarly convert the substrate 5-(4-fluorophenyl) valeric acid into the monomer unit represented by formula (I) derived from corresponding 3-hydroxy-5-(4-fluorophenyl) valeric acid and produce a PHA containing the monomer unit.

Example 4

PHA Production (2) Using a PHA Synthase Gene Recombinant *E. coli*

Each of the pP161-C1 and pP161-C2 recombinant strains was inoculated to 200 mL of M9 medium containing 0.5% yeast extract and 0.2% 4-phenoxybutyric acid(PxBA), and the medium was shaken at 37° C. with a rate of 125 strokes/min. After 24 hours, the cells were collected by centrifugation, washed once with cold methanol and lyophilized.

The lyophilized pellet was suspended in 100 mL of chloroform and the suspension was stirred at 60° C. for 20 hours to extract a PHA. After filtering the extract through a membrane filter with a pore size of 0.45 μm, the filtrate was concentrated by rotary evaporation. Then, the concentrate was re-suspended in cold methanol and the precipitant was collected and dried in vacuo to provide a PHA. The PHA thus obtained was subject to methanolysis as usual and

TABLE 1

|  | pP161-C1 recombinant strain | pP161-C2 recombinant strain |
|---|---|---|
| Cell dry weight | 900 mg/L | 940 mg/L |
| Polymer dry weight | 35 mg/L | 37 mg/L |
| Polymer dry weight/Cell dry weight | 4% | 4% |
| Monomer unit composition (area ratio) | | |
| 3-Hydroxybutyric acid | 0% | 0% |
| 3-Hydroxyvaleric acid | 0% | 0% |
| 3-Hydroxyhexanoic acid | 0% | 0% |
| 3-Hydroxyheptanoic acid | 7% | 5% |
| 3-Hydroxyoctanoic acid | 6% | 5% |
| 3-Hydroxynonanoic acid | 9% | 12% |
| 3-Hydroxydecanoic acid | 12% | 12% |
| 3-Hydroxy-5-(4-fluorophenyl) valeric acid | 66% | 66% |

These results show that both pP161-C1 and pP161-C2 recombinant strains produce, from the substrate 5-(4-fluorophenyl) valeric acid, PHAs comprising a monomer unit represented by formula (I) derived from corresponding 3-hydroxy-5-(4-fluorophenyl) valeric acid as a main component. It is, therefore, demonstrated that although the pP161-C1 and pP161-C2 recombinant strains exclusively analyzed using a gas chromatography-mass spectrometry apparatus (GC-MS, Shimadzu QP-5050, EI technique) to identify methyl-esterified PHA monomer units. Table 2 shows together a cell dry weight, a polymer dry weight for a collected PHA, a polymer yield per a cell (polymer dry weight/cell dry weight) and identities of monomer units for each strain.

TABLE 2

|  | pP161-C1 recombinant strain | pP161-C2 recombinant strain |
|---|---|---|
| Cell dry weight | 750 mg/L | 720 mg/L |
| Polymer dry weight | 4 mg/L | 4 mg/L |
| Polymer dry weight/Cell dry weight | 0.5% | 0.5% |
| Monomer unit composition (area ratio) | | |
| 3-Hydroxybutyric acid | 0% | 0% |
| 3-Hydroxyvaleric acid | 0% | 0% |

TABLE 2-continued

|  | pP161-C1 recombinant strain | pP161-C2 recombinant strain |
|---|---|---|
| 3-Hydroxyhexanoic acid | 0% | 0% |
| 3-Hydroxyheptanoic acid | 2% | 2% |
| 3-Hydroxyoctanoic acid | 3% | 3% |
| 3-Hydroxynonanoic acid | 5% | 7% |
| 3-Hydroxydecanoic acid | 5% | 6% |
| 3-Hydroxy-4-phenoxybutyric acid | 85% | 82% |

These results show that both pP161-C1 and pP161-C2 recombinant strains produce, from the substrate 4-phenoxybutyric acid, PHAs comprising a monomer unit represented by formula (VI) derived from corresponding 3-hydroxy-4-phenoxybutyric acid as a main component. It is, therefore, demonstrated that although the pP161-C1 and pP161-C2 recombinant strains exclusively produce PHA synthases having the amino acid sequences of SEQ ID NOs. 1 and 3 translated from the PHA synthase genes comprising the sequences of SEQ ID NOs. 2 and 4, respectively, both strains similarly convert the substrate 4-phenoxybutyric acid into the monomer unit represented by formula (VI) derived from corresponding 3-hydroxy-4-phenoxybutyric acid and produce a PHA containing the monomer unit.

Example 5

PHA Production (3) Using a PHA Synthase Gene Recombinant E. coli

Each of the pP161-C1 and pP161-C2 recombinant strains was inoculated to 200 mL of M9 medium containing 0.5% yeast extract and 0.1% 6-phenylhexanoic acid (PHxA), and the medium was shaken at 37° C. with a rate of 125 strokes/min. After 24 hours, the cells were collected by centrifugation, washed once with cold methanol and lyophilized.

The lyophilized pellet was suspended in 100 mL of chloroform and the suspension was stirred at 60° C. for 20 hours to extract a PHA. After filtering the extract through a membrane filter with a pore size of 0.45 μm, the filtrate was concentrated by rotary evaporation. Then, the concentrate was re-suspended in cold methanol and the precipitant was collected and dried in vacuo to provide a PHA. The PHA thus obtained was subject to methanolysis as usual and analyzed using a gas chromatography-mass spectrometry apparatus (GC-MS, Shimadzu QP-5050, EI technique) to identify methyl-esterified PHA monomer units. Table 3 shows together a cell dry weight, a polymer dry weight for a collected PHA, a polymer yield per a cell (polymer dry weight/cell dry weight) and identities of monomer units for each strain.

TABLE 3

|  | pP161-C1 recombinant strain | pP161-C2 recombinant strain |
|---|---|---|
| Cell dry weight | 1050 mg/L | 980 mg/L |
| Polymer dry weight | 73 mg/L | 70 mg/L |
| Polymer dry weight/Cell dry weight | 7% | 7% |
| Monomer unit composition (area ratio) |  |  |
| 3-Hydroxybutyric acid | 0% | 0% |
| 3-Hydroxyvaleric acid | 0% | 0% |
| 3-Hydroxyhexanoic acid | 0% | 0% |
| 3-Hydroxyheptanoic acid | 3% | 3% |
| 3-Hydroxyoctanoic acid | 3% | 4% |
| 3-Hydroxynonanoic acid | 5% | 2% |
| 3-Hydroxydecanoic acid | 5% | 4% |
| 3-Hydroxy-6-phenylhexanoic acid | 84% | 87% |

These results show that both pP161-C1 and pP161-C2 recombinant strains produce, from the substrate 6-phenylhexanoic acid, PHAs comprising a monomer unit represented by formula (IX) derived from corresponding 3-hydroxy-6-phenylhexanoic acid as a main component. It is, therefore, demonstrated that although the pP161-C1 and pP161-C2 recombinant strains exclusively produce PHA synthases having the amino acid sequences of SEQ ID NOs. 1 and 3 translated from the PHA synthase genes comprising the sequences of SEQ ID NOs. 2 and 4, respectively, both strains similarly convert the substrate 6-phenylhexanoic acid into the monomer unit represented by formula (IX) derived from corresponding 3-hydroxy-6-phenylhexanoic acid and produce a PHA containing the monomer unit.

The results together with those in Examples 3 and 4 demonstrate that the PHA synthases having the amino acid sequences of SEQ ID NOs. 1 and 3 have enzyme activity mutually similar in substrate specificity.

SEQUENCE LISTING

<160> NUMBER OF SEQ ID NOS: 11

<210> SEQ ID NO 1
<211> LENGTH: 559
<212> TYPE: PRT
<213> ORGANISM: Pseudomonas jessenii P161 ; FERM BP-7376

<400> SEQUENCE: 1

Met Ser Asn Lys Asn Asn Asp Asp Leu Lys Ser Gln Ala Ser Glu
 1               5                  10                  15

Asn Thr Leu Gly Leu Asn Pro Val Val Gly Leu Arg Gly Lys Asp
                20                  25                  30

Leu Leu Ala Ser Ala Arg Met Val Leu Arg Gln Ala Ile Lys Gln
                35                  40                  45

Pro Ile His Ser Ala Arg His Val Ala His Phe Gly Leu Glu Leu
                50                  55                  60

Lys Asn Val Leu Gly Lys Ser Glu Leu Leu Pro Thr Ser Asp
                65                  70                  75

Asp Arg Arg Phe Ala Asp Pro Ala Trp Ser Gln Asn Pro Leu Tyr
                80                  85                  90

Lys Arg Tyr Leu Gln Thr Tyr Leu Ala Trp Arg Lys Glu Leu His
                95                 100                 105

Asp Trp Ile Asp Ser Asn Leu Pro Ala Lys Asp Val Ser Arg
               110                 115                 120

Gly His Phe Val Ile Asn Leu Met Thr Glu Ala Phe Ala Pro Thr
               125                 130                 135

Asn Thr Ala Ala Asn Pro Ala Ala Val Lys Arg Phe Phe Glu Thr
               140                 145                 150

Gly Gly Lys Ser Leu Leu Asp Gly Leu Ser His Leu Ala Lys Asp
               155                 160                 165

Leu Val His Asn Gly Gly Met Pro Ser Gln Val Asn Met Gly Ala
               170                 175                 180

Phe Glu Val Gly Lys Thr Leu Gly Val Thr Glu Gly Ala Val Val
               185                 190                 195

Phe Arg Asn Asp Val Leu Glu Leu Ile Gln Tyr Lys Pro Ile Thr
               200                 205                 210

Glu Gln Val His Glu Arg Pro Leu Leu Val Pro Pro Gln Ile
               215                 220                 225

Asn Lys Phe Tyr Val Phe Asp Leu Ser Pro Glu Lys Ser Leu Ala
               230                 235                 240

Arg Phe Cys Leu Arg Asn Asn Val Gln Thr Phe Ile Val Ser Trp
               245                 250                 255

Arg Asn Pro Thr Lys Glu Gln Arg Glu Trp Gly Leu Ser Thr Tyr
               260                 265                 270

Ile Glu Ala Leu Lys Glu Ala Val Asp Val Thr Ala Ile Thr
               275                 280                 285

Gly Ser Lys Asp Val Asn Met Leu Gly Ala Cys Ser Gly Gly Ile
               290                 295                 300

Thr Cys Thr Ala Leu Leu Gly His Tyr Ala Ala Ile Gly Glu Asn
               305                 310                 315

Lys Val Asn Ala Leu Thr Leu Leu Val Ser Val Leu Asp Thr Thr
               320                 325                 330

Leu Asp Ser Asp Val Ala Leu Phe Val Asp Glu Gln Thr Leu Glu

```
                335                 340                 345
Ala Ala Lys Arg Gln Ser Tyr Gln Ala Gly Val Leu Glu Gly Arg
                350                 355                 360
Asp Met Ala Lys Val Phe Ala Trp Met Arg Pro Asn Asp Leu Ile
                365                 370                 375
Trp Asn Tyr Trp Val Asn Asn Tyr Leu Leu Gly Asn Glu Pro Pro
                380                 385                 390
Val Phe Asp Ile Leu Phe Trp Asn Asn Asp Thr Thr Arg Leu Pro
                395                 400                 405
Ala Ala Phe His Gly Asp Leu Ile Glu Met Phe Lys Ser Asn Pro
                410                 415                 420
Leu Thr Arg Ala Asp Ala Leu Glu Val Cys Gly Thr Pro Ile Asp
                425                 430                 435
Leu Lys Lys Val Thr Ala Asp Ile Phe Ser Leu Ala Gly Thr Ser
                440                 445                 450
Asp His Ile Thr Pro Trp Arg Ser Cys Tyr Lys Ser Ala Gln Leu
                455                 460                 465
Phe Gly Gly Asn Val Glu Phe Val Leu Ser Ser Ser Gly His Ile
                470                 475                 480
Gln Ser Ile Leu Asn Pro Pro Gly Asn Pro Lys Ser Arg Tyr Met
                485                 490                 495
Thr Ser Thr Glu Met Pro Ala Asn Ala Asp Asp Trp Gln Glu Glu
                500                 505                 510
Ser Thr Lys His Ala Asp Ser Trp Trp Leu His Trp Gln Ala Trp
                515                 520                 525
Gln Ala Gln Arg Ser Gly Asn Leu Lys Lys Ala Pro Leu Lys Leu
                530                 535                 540
Gly Asn Lys Ala Tyr Pro Ala Gly Glu Ala Ala Pro Gly Thr Tyr
                545                 550                 555
Val His Glu Arg

<210> SEQ ID NO 2
<211> LENGTH: 1680
<212> TYPE: DNA
<213> ORGANISM: Pseudomonas jessenii P161 ; BP-7376

<400> SEQUENCE: 2
atgagtaaca agaataacga tgacttgaag agtcaagcct cggaaaacac         50
cttggggctg aatcctgtcg ttggactgcg tggaaaggat ctactggctt        100
ctgctcgaat ggtgctcagg caggccatca agcaaccgat tcacagcgcc        150
aggcatgtcg ctcatttcgg cctggaactc aagaacgtgc tgctcggcaa        200
atccgagctg ctaccgacca gcgatgaccg tcgtttcgcg gatccggcct        250
ggagccagaa cccgctctac aaacgttatc tgcaaaccta cctggcgtgg        300
cgcaaggaac tccacgactg gatcgacgac agcaacctgc cggccaagga        350
cgtcagccgc gggcacttcg tgatcaacct catgaccgag gccttcgccc        400
cgaccaacac ggcggccaac ccggcggcgg tcaaacgctt cttcgaaacc        450
ggtggcaaga gcctgctcga tggcctctcg catctggcca aggacctggt        500
acataacggc ggcatgccga gccaggtcaa catgggcgca ttcgaggtcg        550
gcaagaccct tggcgtgacc gagggcgcgg tggtctttcg caatgacgtg        600
ctggaactga tccagtacaa accgatcacc gagcaggtgc atgaacgccc        650
```

| | |
|---|---|
| actgctggtg gtaccgccac agatcaacaa gttctacgtt ttcgacctga | 700 |
| gcccggaaaa gagcctggcg cgattctgcc tgcgcaacaa cgtgcagacc | 750 |
| ttcatcgtca gctggcgcaa cccgaccaag gagcagcgcg agtggggcct | 800 |
| gtcgacctac atcgaagcgc tcaaggaagc ggttgatgtg gtcaccgcca | 850 |
| tcaccggcag caaagacgtg aacatgctcg gtgcctgctc cggcggcatc | 900 |
| acctgcaccg cgctgctggg ccactacgca gcaatcggcg agaacaaggt | 950 |
| caacgccctg accctgctgg tcagcgtgct cgacaccacc ctggacagcg | 1000 |
| acgtggccct gttcgtcgac gagcagaccc tcgaagccgc caagcgccag | 1050 |
| tcgtaccagg ccggtgtact cgaaggccgt gacatggcga agtcttcgc | 1100 |
| ctggatgcgc ccaacgacc tgatctggaa ctactgggtc aacaactact | 1150 |
| tgttgggcaa cgagccgccg gtattcgaca ttctgttctg gaacaacgac | 1200 |
| accacccggt tgcccgccgc gttccatggc gacctgatcg agatgttcaa | 1250 |
| aagtaacccg ttgacccgtg ccgatgcact ggaagtgtgc ggtacgccga | 1300 |
| tcgatctgaa gaaagtcacc gccgacatct ctcgctggc cggcaccagc | 1350 |
| gaccacatta cccgtggcg ctcctgctac aagtcggcgc aactgttcgg | 1400 |
| cggcaacgtt gaattcgtat tgtccagcag cgggcacatc cagagcattc | 1450 |
| tgaacccgcc gggcaatccg aaatcgcgtt acatgaccag caccgaaatg | 1500 |
| cccgccaatg ccgatgactg gcaggaagag tcgaccaagc acgccgactc | 1550 |
| ctggtggctg cactggcagg catggcaggc acagcgttcg ggcaacctga | 1600 |
| aaaaagcccc gctgaaattg ggcaacaagg cctatccagc gggtgaagcc | 1650 |
| gcaccgggca cttacgtgca tgagcggtaa | 1680 |

<210> SEQ ID NO 3
<211> LENGTH: 560
<212> TYPE: PRT
<213> ORGANISM: Pseudomonas jessenii P161 ; BP-7376

<400> SEQUENCE: 3

```
Met Arg Glu Lys Pro Ala Arg Asp Ser Leu Pro Thr Pro Ala Ala
  1               5                  10                  15

Phe Ile Asn Ala Gln Ser Ala Ile Thr Gly Leu Arg Gly Arg Asp
                 20                  25                  30

Leu Leu Ser Thr Leu Arg Ser Val Ala Ala His Gly Leu Arg Asn
                 35                  40                  45

Pro Val His Ser Ala Arg His Ala Leu Lys Leu Gly Gly Gln Leu
                 50                  55                  60

Gly Arg Val Leu Leu Gly Glu Thr Leu His Pro Thr Asn Pro Gln
                 65                  70                  75

Asp Thr Arg Phe Ala Asp Pro Ala Trp Ser Leu Asn Pro Phe Tyr
                 80                  85                  90

Arg Arg Ser Leu Gln Ala Tyr Leu Ser Trp Gln Lys Gln Val Lys
                 95                 100                 105

Ser Trp Ile Asp Glu Ser Asn Met Ser Pro Asp Arg Ala Arg
                110                 115                 120

Ala His Phe Ala Phe Ala Leu Leu Asn Asp Ala Val Ser Pro Ser
                125                 130                 135

Asn Thr Leu Leu Asn Pro Leu Ala Val Lys Glu Phe Phe Asn Ser
```

-continued

```
                140                 145                 150
Gly Gly Asn Ser Leu Val Arg Gly Ile Gly His Leu Val Asp Asp
            155                 160                 165
Leu Leu His Asn Asp Gly Leu Pro Arg Gln Val Thr Lys Gln Ala
            170                 175                 180
Phe Glu Val Gly Lys Thr Val Ala Thr Thr Gly Ala Val Val
            185                 190                 195
Phe Arg Asn Glu Leu Leu Glu Leu Ile Gln Tyr Lys Pro Met Ser
            200                 205                 210
Glu Lys Gln Tyr Ser Lys Pro Leu Leu Val Pro Pro Gln Ile
            215                 220                 225
Asn Lys Tyr Tyr Ile Phe Asp Leu Ser Pro His Asn Ser Phe Val
            230                 235                 240
Gln Tyr Ala Leu Lys Asn Gly Leu Gln Thr Phe Met Ile Ser Trp
            245                 250                 255
Arg Asn Pro Asp Val Arg His Arg Glu Trp Gly Leu Ser Thr Tyr
            260                 265                 270
Val Glu Ala Val Glu Ala Met Asn Val Cys Arg Ala Ile Thr
            275                 280                 285
Gly Ala Arg Glu Val Asn Leu Met Gly Ala Cys Ala Gly Gly Leu
            290                 295                 300
Thr Ile Ala Ala Leu Gln Gly His Leu Gln Ala Lys Arg Gln Leu
            305                 310                 315
Arg Arg Val Ser Ser Ala Thr Tyr Leu Val Ser Leu Leu Asp Ser
            320                 325                 330
Glu Leu Asp Ser Pro Ala Ser Leu Phe Ala Asp Glu Gln Thr Leu
            335                 340                 345
Glu Ala Ala Lys Arg Arg Ser Tyr Gln Lys Gly Val Leu Asp Gly
            350                 355                 360
Arg Asp Met Ala Lys Val Phe Ala Trp Met Arg Pro Asn Asp Leu
            365                 370                 375
Ile Trp Ser Tyr Phe Val Asn Asn Tyr Leu Leu Gly Lys Glu Pro
            380                 385                 390
Pro Ala Phe Asp Ile Leu Tyr Trp Asn Asn Asp Ser Thr Arg Leu
            395                 400                 405
Pro Ala Ala Leu His Gly Asp Leu Leu Asp Phe Phe Lys His Asn
            410                 415                 420
Pro Leu Thr His Pro Gly Gly Leu Glu Val Cys Gly Thr Pro Ile
            425                 430                 435
Asp Leu Gln Lys Val Thr Val Asp Ser Phe Ser Val Ala Gly Ile
            440                 445                 450
Asn Asp His Ile Thr Pro Trp Asp Ala Val Tyr Arg Ser Ala Leu
            455                 460                 465
Leu Leu Gly Gly Glu Arg Arg Phe Val Leu Ser Asn Ser Gly His
            470                 475                 480
Val Gln Ser Ile Leu Asn Pro Pro Ser Asn Pro Lys Ala Asn Tyr
            485                 490                 495
Val Glu Asn Gly Lys Leu Ser Ser Asp Pro Arg Ala Trp Tyr Tyr
            500                 505                 510
Asp Ala Arg His Val Asp Gly Ser Trp Trp Thr Gln Trp Leu Ser
            515                 520                 525
Trp Ile Gln Glu Arg Ser Gly Ala Gln Lys Glu Thr His Met Ala
            530                 535                 540
```

-continued

Leu Gly Asn Gln Asn Tyr Pro Pro Met Glu Ala Ala Pro Gly Thr
            545                 550                 555

Tyr Val Arg Val Arg
            560

<210> SEQ ID NO 4
<211> LENGTH: 1683
<212> TYPE: DNA
<213> ORGANISM: Pseudomonas jessenii P161 ; BP-7376

<400> SEQUENCE: 4

| | | |
|---|---|---|
| atgcgcgaga aaccagcgag ggattcctta ccgactcccg ccgcgttcat | 50 |
| caatgcacag agtgcgatta ccggcctgcg cggtcgggat ctgttatcga | 100 |
| ccctgcgtag tgtggccgcc catggcttgc gcaatccggt gcacagtgcc | 150 |
| cgacatgccc tcaaactcgg cggccagctc ggtcgtgtgt tgctgggcga | 200 |
| aaccctgcac ccgaccaacc cgcaggacac tcgcttcgcc gatccggcgt | 250 |
| ggagcctcaa cccgttttat cggcgcagcc tgcaggctta tctgagctgg | 300 |
| cagaagcagg tcaaaagctg gatcgacgag agcaacatga gcccggacga | 350 |
| ccgtgcccgc gcccacttcg ctttcgcctt gctcaacgac gccgtatcgc | 400 |
| cctccaacac cctgctcaat ccattggcgg tcaaggagtt cttcaattcc | 450 |
| gggggtaaca gcctggtgcg tggcatcggc atctggtgg acgatctgct | 500 |
| gcacaacgat ggcctgcccc ggcaagtcac caagcaagcg ttcgaggtcg | 550 |
| gcaagacggt cgccaccacc accggtgccg tggtgtttcg caacgaactg | 600 |
| ctggagttga tccagtacaa gccgatgagc gaaaagcagt attccaagcc | 650 |
| cctgttggtg gtgccgccgc aaatcaacaa gtactacatt ttcgacctga | 700 |
| gcccccacaa cagcttcgtc cagtacgcgc tgaaaaacgg cctgcaaacc | 750 |
| ttcatgatca gctggcgcaa cccggatgtg cgtcaccgcg aatggggct | 800 |
| ctcgacctac gtggaagccg tggaagaagc catgaatgtc tgccgggcga | 850 |
| tcaccggtgc acgcgaggtc aacctgatgg gcgcctgcgc cggcgggctg | 900 |
| accattgccg cgttgcaggg ccacttgcaa gccaaacggc agctgcgcag | 950 |
| ggtgtccagt gcaacgtatc tggtgagcct gctcgacagt gaactggaca | 1000 |
| gccccgcttc actgttcgcc gacgaacaga ctctggaggc tgccaagcgt | 1050 |
| cgctcctatc agaaaggtgt gctggacggc gcgacatgg ccaaggtctt | 1100 |
| cgcctggatg cgccccaacg atttgatctg gagctacttc gtcaacaact | 1150 |
| acctgttggg caaggagccg ccggcgttcg acatcctcta ctggaacaac | 1200 |
| gacagcacgc gcttgcctgc cgccctgcat ggcgacctgc tggacttctt | 1250 |
| caagcacaac ccgctgaccc acccgggcgg cctggaagtg tgtggcacgc | 1300 |
| cgatcgattt gcagaaggtc accgttgaca gcttcagcgt cgccggcatc | 1350 |
| aacgatcaca tcacgccttg ggatgcggtg tatcgctcgg cgctgttgct | 1400 |
| cggtggcgag cggcgcttcg tgctgtccaa cagcggccat gtgcagagca | 1450 |
| tcctcaaccc gccgagcaac ccgaaagcca actacgtcga aaacggcaag | 1500 |
| ctgagcagcg accccgcgc ctggtactac gacgccaggc atgtcgacgg | 1550 |
| cagttggtgg acccaatggc tgagctggat tcaggaacgc tccggcgcgc | 1600 |

-continued

| agaaggaaac ccacatggcg ctcggcaacc agaactatcc accgatggaa | 1650 |
| gctgcgcccg gtacctacgt acgtgtgcgc tga | 1683 |

<210> SEQ ID NO 5
<211> LENGTH: 1501
<212> TYPE: DNA
<213> ORGANISM: Pseudomonas jessenii P161 ; BP-7376
<220> FEATURE:

<400> SEQUENCE: 5

| tgaacgctgg cggcaggcct aacacatgca agtcgagcgg atgacgggag | 50 |
| cttgctcctg aattcagcgg cggacgggtg agtaatgcct aggaatctgc | 100 |
| ctggtagtgg gggacaacgt ctcgaaaggg acgctaatac cgcatacgtc | 150 |
| ctacgggaga aagcagggga ccttcgggcc ttgcgctatc agatgagcct | 200 |
| aggtcggatt agctagttgg tgaggtaatg gctcaccaag gcgacgatcc | 250 |
| gtaactggtc tgagaggatg atcagtcaca ctggaactga gacacggtcc | 300 |
| agactcctac gggaggcagc agtggggaat attggacaat gggcgaaagc | 350 |
| ctgatccagc catgccgcgt gtgtgaagaa ggtcttcgga ttgtaaagca | 400 |
| ctttaagttg ggaggaaggg cattaaccta atacgttagt gttttgacgt | 450 |
| taccgacaga ataagcaccg gctaactctg tgccagcagc cgcggtaata | 500 |
| cagagggtgc aagcgttaat cggaattact gggcgtaaag cgcgcgtagg | 550 |
| tggtttgtta agttggatgt gaaagccccg ggctcaacct gggaactgca | 600 |
| ttcaaaactg acaagctaga gtatggtaga gggtggtgga atttcctgtg | 650 |
| tagcggtgaa atgcgtagat ataggaagga acaccagtgg cgaaggcgac | 700 |
| cacctggact gatactgaca ctgaggtgcg aaagcgtggg gagcaaacag | 750 |
| gattagatac cctggtagtc cacgccgtaa acgatgtcaa ctagccgttg | 800 |
| ggagccttga gctcttagtg gcgcagctaa cgcattaagt tgaccgcctg | 850 |
| gggagtacgg ccgcaaggtt aaaactcaaa tgaattgacg ggggcccgca | 900 |
| caagcggtgg agcatgtggt ttaattcgaa gcaacgcgaa gaaccttacc | 950 |
| aggccttgac atccaatgaa ctttccagag atggatgggt gccttcggga | 1000 |
| acattgagac aggtgctgca tggctgtcgt cagctcgtgt cgtgagatgt | 1050 |
| tgggttaagt cccgtaacga gcgcaaccct tgtccttagt taccagcacg | 1100 |
| taatggtggg cactctaagg agactgccgg tgacaaaccg gaggaaggtg | 1150 |
| gggatgacgt caagtcatca tggcccttac ggcctgggct acacacgtgc | 1200 |
| tacaatggtc ggtacagagg gttgccaagc cgcgaggtgg agctaatccc | 1250 |
| acaaaaccga tcgtagtccg gatcgcagtc tgcaactcga ctgcgtgaag | 1300 |
| tcggaatcgc tagtaatcgc gaatcagaat gtcgcggtga atacgttccc | 1350 |
| gggccttgta cacaccgccc gtcacaccat gggagtgggt tgcaccagaa | 1400 |
| gtagctagtc taaccttcgg gaggacggtt accacggtgt gattcatgac | 1450 |
| tggggtgaag tcgtaccaag gtagccgtag gggaacctgc ggctggatca | 1500 |
| c | 1501 |

<210> SEQ ID NO 6
<211> LENGTH: 20
<212> TYPE: DNA

```
<213> ORGANISM: Artificial Sequence
<220> FEATURE:
<223> OTHER INFORMATION: Primer for PCR multiplication

<400> SEQUENCE: 6
tgctggaact gatccagtac                                                    20

<210> SEQ ID NO 7
<211> LENGTH: 23
<212> TYPE: DNA
<213> ORGANISM: Artificial Sequence
<220> FEATURE:
<223> OTHER INFORMATION: Primer for PCR multiplication

<400> SEQUENCE: 7
gggttgagga tgctctggat gtg                                                23

<210> SEQ ID NO 8
<211> LENGTH: 30
<212> TYPE: DNA
<213> ORGANISM: Artificial Sequence
<220> FEATURE:
<223> OTHER INFORMATION: Primer for PCR multiplication

<400> SEQUENCE: 8
ctacaaagct tgacccggta ctcgtctcag                                         30

<210> SEQ ID NO 9
<211> LENGTH: 29
<212> TYPE: DNA
<213> ORGANISM: Artificial Sequence
<220> FEATURE:
<223> OTHER INFORMATION: Primer for PCR multiplication

<400> SEQUENCE: 9
gcgagcaagc ttgctcctac agggatagc                                          29

<210> SEQ ID NO 10
<211> LENGTH: 29
<212> TYPE: DNA
<213> ORGANISM: Artificial Sequence
<220> FEATURE:
<223> OTHER INFORMATION: Primer for PCR multiplication

<400> SEQUENCE: 10
gttttaagct tgaagacgaa ggagtgttg                                          29

<210> SEQ ID NO 11
<211> LENGTH: 30
<212> TYPE: DNA
<213> ORGANISM: Artificial Sequence
<220> FEATURE:
<223> OTHER INFORMATION: Primer for PCR multiplication

<400> SEQUENCE: 11
ctcctacaag cttggagact gactgtggcc                                         30
```

What is claimed is:

1. An isolated polyhydroxyalkanoate synthase having an amino acid sequence of SEQ ID NO: 1.

* * * * *

UNITED STATES PATENT AND TRADEMARK OFFICE
CERTIFICATE OF CORRECTION

PATENT NO. : 6,485,951 B2  
DATED : November 26, 2002  
INVENTOR(S) : Tetsuya Yano et al.

It is certified that error appears in the above-identified patent and that said Letters Patent is hereby corrected as shown below:

Column 4,  
Line 1, "(PXBA)" should read -- (PxBA) --;  
Line 39, "PXBA" should read -- PxBA --; and  
Line 60, "PXBA" should read -- PxBA --.

Column 7,  
Line 34, "strain and" should read -- strain, exhibiting --;  
Line 35, "exhibits" should be deleted; and "it selectively produces" should be deleted;  
Line 38, "structure." should read -- structure is produced. --;  
Line 55, "covert" should read -- convent --; and  
Line 57, "(PXBA)" should read -- (PxBA) --.

Column 8,  
Line 45, "automonouosly" should read -- autonomously --.

Column 9,  
Line 30, "but" should read -- but are --.

Column 10,  
Line 21, "(Parkin" should read -- (Perkin --.

Column 14,  
Line 41, "fragment" should read -- fragments --.

Column 29, [Sequence List-continued]  
"<220> FEATURE:" should read  
--
<220> FEATURE:  
  <223> OTHER INFORMATION: cDNA to 165 rNA --.

Signed and Sealed this

Nineteenth Day of August, 2003

JAMES E. ROGAN  
*Director of the United States Patent and Trademark Office*